Figure 1:
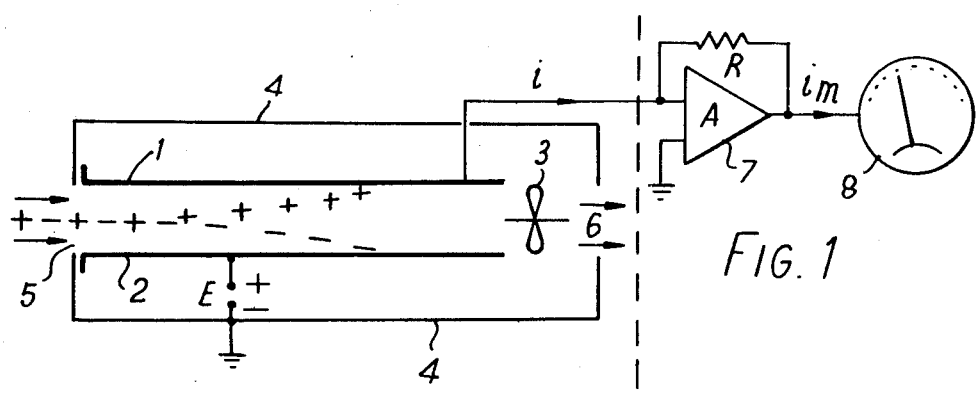

United States Patent [19]

Laws

[11] 4,114,088
[45] Sep. 12, 1978

[54] ATMOSPHERIC ION DENSITY MEASUREMENT

[75] Inventor: Christopher Malcolm Laws, Old Oxted, England

[73] Assignee: Cecil Alfred Laws, England

[21] Appl. No.: 772,646

[22] Filed: Feb. 28, 1977

[51] Int. Cl.² .............................................. G01N 27/00
[52] U.S. Cl. ................................ 324/33; 324/71 R; 73/194 F
[58] Field of Search ................ 324/33, 71 R, 71 CP; 340/237 R, 237 S; 361/230; 73/194 F; 250/282, 287, 489

[56] References Cited

U.S. PATENT DOCUMENTS

| | | | |
|---|---|---|---|
| 3,835,705 | 9/1974 | Hadjidjanian | 73/194 F |
| 3,889,180 | 6/1975 | Eichmeier | 324/33 |
| 3,986,111 | 10/1976 | Sellers | 324/71 R |
| 4,003,254 | 1/1977 | Bullis et al. | 73/194 F |

*Primary Examiner*—Rudolph V. Rolinec
*Assistant Examiner*—Vincent J. Sunderdick

[57] ABSTRACT

An ion counter for measuring the density of atmospheric ions has two basic sections, the electrometer, which is of a conventional type, and the collector. An improved collector is provided having two collector plates in electrical contact, mounted either side of a polarizing plate to form a double channel cell having two air passages. The polarizing plate and the collector plates are tightly secured to insulators so as accurately to maintain the spacing between the plates.

10 Claims, 8 Drawing Figures

ATMOSPHERIC ION DENSITY MEASUREMENT

This invention relates to the design of instruments for measuring the density of atmospheric ions.

Air-ions are described as air molecules which, due to the acquisition or loss of an electron, carry a net negative or positive charge respectively. Air ionization occurs in nature as a result of radio-active elements in the soil and the air, ultra-violet and other radiations, friction effects, lightning, etc. Typically, clean country air contains between 1000 and 2000 ions/cm with mobilities $\geq$ 0.04 cm$^2$/sec.V. These are the so-called Small and Medium ions. When air becomes polluted, as in cities, the particulate matters (smoke, dust, fumes, etc.) act as condensation muclei to which the Small and Medium ions adhere in clusters to form Large ions with mobilities of $<$ 0.001 cm$^2$/sec.V. Instruments for measuring the incidence or density of air-ions are largely termed Ion Counters, or Ion Density Meters, and are usually calibrated to give the number of ions, or ion charges, per cubic centimeter.

The present invention provides an ion counter for measuring the density of atmospheric ions having two basic sections; the electrometer, which is of a conventional type, and the collector. An improved collector is provided having two collector plates in electrical contact, mounted either side of a polarizing plate to form a double channel cell having two air passages. The polarizing plate and the collector plates are tightly secured to insulators so as accurately to maintain the spacing between the plates.

Figure 2:
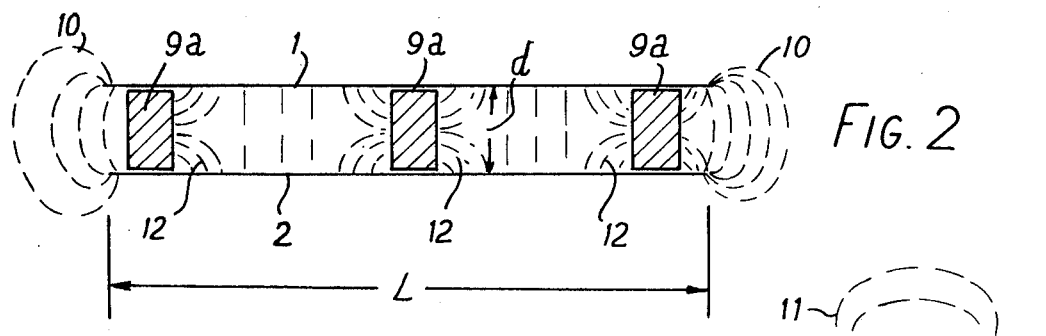
Figure 3:
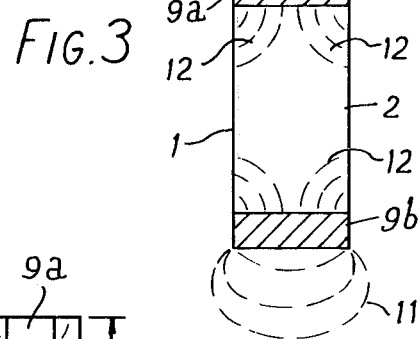
Figure 4:
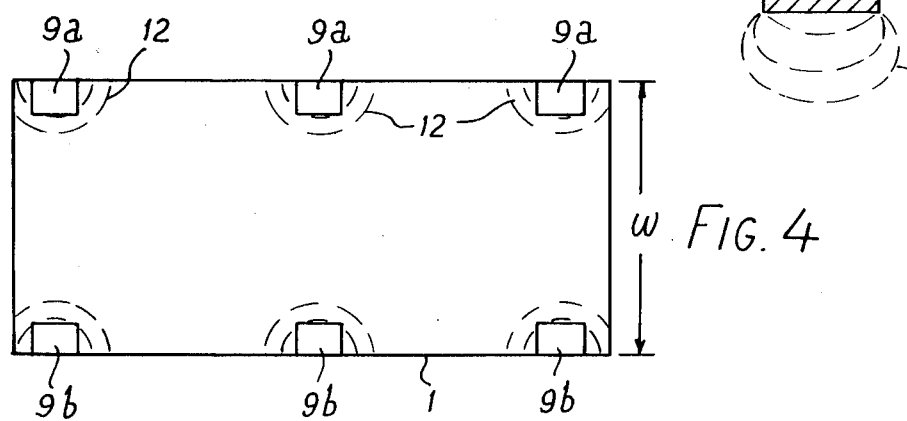
Figure 5:
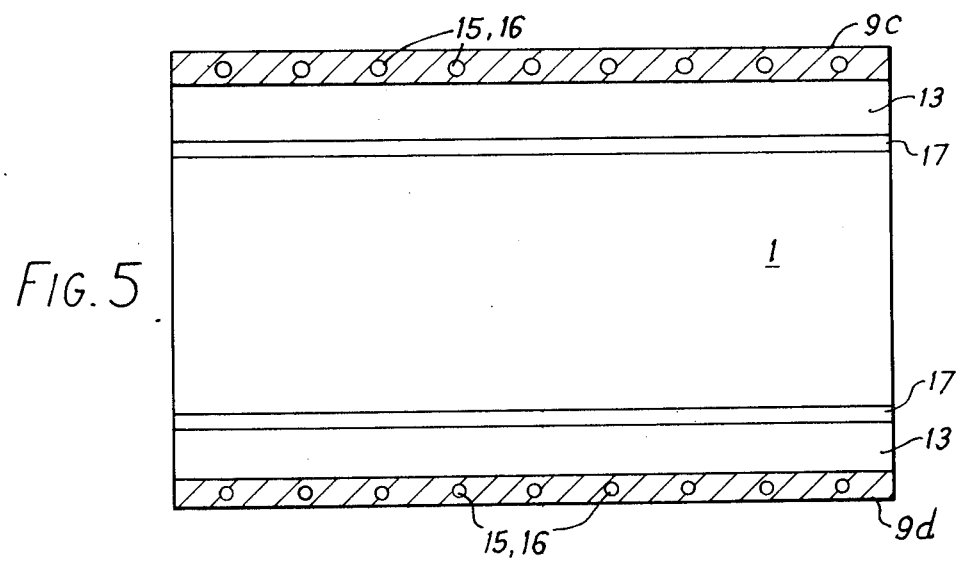
Figure 7:
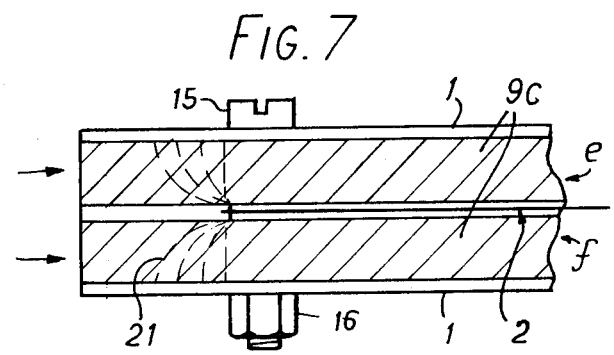
Figure 6:
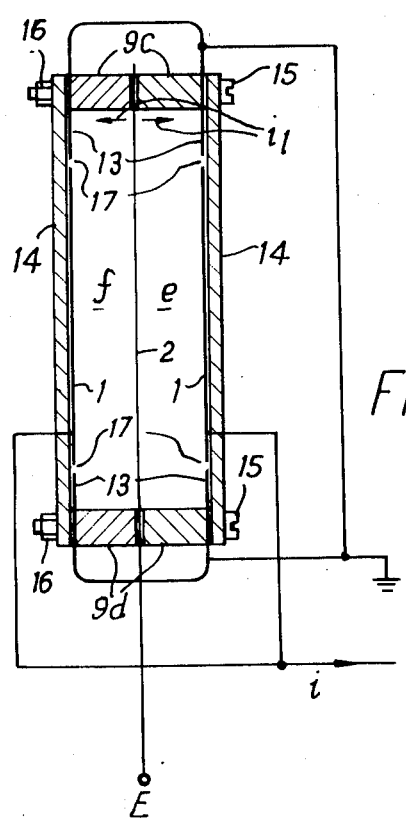
Figure 8:
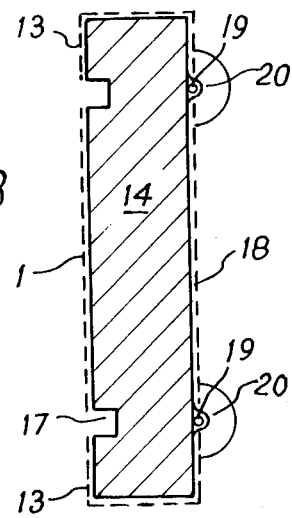

An embodiment of the invention and the purpose thereof will now be described, by way of example, with reference to the accompanying drawings, of which:

FIG. 1 is a view illustrating the principles of the improved instrument for measuring the density of atmospheric ions in accordance with the present invention;

FIGS. 2, 3, and 4 are views illustrating the essential constructional elements in a typical collector of the improved instrument for measuring the density of atmospheric ions in accordance with the present invention;

FIGS. 5, 6, and 7 are views illustrating the improved design of a typical collector of the improved instrument for measuring the density of atmospheric ions in accordance with the present invention; and FIG. 8 is a view illustrating additional features of the constructional details of one embodiment of a typical collector of the improved instrument for measuring the density of atmospheric ions in accordance with the present invention.

The principles of the type of Ion Counter with which this invention is concerned will now be briefly described with reference to FIG. 1.

The instrument has two basic sections which will be termed the Collector and the Electrometr. The Collector, which may take any one of a number of forms, comprises in this example two flat conductive plates 1 and 2, suitably spaced, a fan 3, and a housing 4 having an inlet port 5, coincident with one open end of plates 1 and 2, and an outlet port 6.

The Electrometer is of conventional type and, in this example, is arranged to measure a very small input current $i$ from a very high impedance source and to provide a larger proportional current $i_m$ to a low impedance meter 8. In this way, the deflection of meter 8 will be a measure of of input current $i$.

In operation, the fan 3 is arranged to draw air at a known velocity $v$ through the space between plates 1 and 2, the air entering at port 5 and leaving at port 6. Plate 2, known as the Polarizing Plate, is held at a steady polarizing potential E.

Plate 1, known as the Collector Plate, is connected to the input of the electrometer amplifier 7, which is maintained at substantially zero potential. An electrostatic field therefore exists between plates 1 and 2 of direction and strength proportional to the size and magnitude of the polarizing potential E. Air ions entering port 5 will therefore be deflected towards plate 1 or 2 depending on whether they carry a positive or negative charge. In FIG. 1, E is made positive so that negative ions are deflected to plate 2 and positive ions to plate 1. The ion current $i$, collected by plate 1 is passed to amplifier 7 and a proportional deflection is given on meter 8. Since the quantity of electricity corresponding to one electron charge is known, and the volume of air passing between plates 1 and 2 is also known, the meter 8 can be calibrated in ions/cm$^3$ on the basis of one charge per ion. The proportion of the total ion content collected by the plates is determined, for a given collector geometry and polarizing potential, by the mobility distribution of the ions in question. Since there is no available method of producing a known and controlled density of atmospheric ions for calibration purposes, it will be apparent that the calibration must be arrived at theoretically from a consideration of the physical parameters of the collector, the established value of an electron charge, the required mobility range and the air velocity.

The present invention is concerned with the design of a Collector which is accurately and reliably amenable to calculation and which will meet the following requirements:

(i) To be capable of accurate theoretical calibration.
(ii) To be rugged in construction so as to retain its calibration indefinitely.
(iii) To cover any defined mobility range.
(iv) To be sufficiently compact and free from external field effects for incorporation in a small portable instrument.
(v) To be easily serviceable.

A collector can be defined by its sensitivity and limiting mobility. Sensitivity, $s$, may be expressed in terms of the current obtained per unit ion density:

$$s = I/\rho = e\phi \qquad (1)$$

where $e = 1.6 \times 10^{-19}$ C, $\phi$ is the air flow (cm$^3$/sec) through the collector, and $\rho$ is the ion density. Since air flow, $\phi$ is given by:

$$\phi = nwdv \qquad (2)$$

where $w$ is the plate width, $n$ the number of collection channels, $d$ the plate spacing and $v$ the air velocity, the sensitivity can be restated as:

$$s = wvdne \qquad (3)$$

The limiting mobility, $K_o$, is given by:

$$K_o = (vd^2)/(EL) \qquad (4)$$

where $E$ is the polarizing potential and $L$ is the plate length. The parameters on which the calibration accuracy and consistency depend are therefore those represented in equations (3) and (4). In addition, since minute currents with a near infinite source impedance are being measured, the preservation of extremely high insulation resistance and the virtual elimination of leakage currents between the polarizing and collector plates are of crucial importance.

Some of the factors which make requirements (i) to (v) difficult to attain are indicated below with reference to the parameters in equations (3) and (4) and to FIGS. 2, 3 and 4 which represent the essential constructional elements in a typical collector. The number of plates, which determines the number of measuring channels ($n$ in equations 2 and 3) has been limited to two for the sake of clarity.

Table 1

| Physical Parameter | Limitations to determination of effective value |
|---|---|
| A. Plate width w | i) Field edge-effects 11. <br> ii) Masking by insulators 9a and 9b. <br> iii) Field 12 due to acquired random charges by insulators 9a and 9b. |
| B. Plate length L | i) Field edge-effects 10. <br> ii) as in A. <br> iii) as in A. |
| C. Plate spacing 'd' | i) Rigidity and flatness of plate. <br> ii) Non-uniformity of field due to fringe effects and random charges on insulators. |
| D. Effective Air Velosity | i) Turbulence due to masking of insulators 9a and 9b. <br> ii) Air-flow distortion along edges of plates open to adjacent spaces. |
| E. Effective Ion Density | i) Deflection of ions from air entering duct by external field from polarizing plate. <br> ii) Random ion current from surrounding still air to outer surface of collector plate. |
| F. Measured Ion Current | i) Leakage current between polarizing and collector plates. <br> ii) General leakage currents from collector plates. |

IMPROVED COLLECTOR DESIGN

An improved design of collector, forming the subject of this invention, will now be described with reference to FIGS. 5, 6 and 7. Two collector plates 1, in electrical contact are mounted on either side of a polarizing plate 2 to form a double channel cell having air passages $f$ and $e$. Polarizing plate 2 is mounted between two insulator strips 9c and two further insulator strips 9d running the full length of the plate. Collector plates 1 are mounted on an insulated plate 14, secured to insulator strips 9c and 9d by a series of bolts 15 and nuts 16, which serve to clamp the complete cell into a rigid assembly. Since insulator strips 9c and 9d have accurately machined surfaces, and plates 1 and 2 are secured to them at frequent intervals along their length, the flatness and spacing of the plates is accurately maintained. Collector plates 1, which do not extend to the edges of mounting plate 14, are separated by a small gap 17 from four plates 13 which are electrically connected and extend to the edges of plate 14.

Plates 13 are maintained at the same potential as plates 1, normally at earth potential, and serve as "guard rings". The surfaces of insulators 9c and 9d are coated with a material which is very slightly conductive so that a tiny leakage current $i_L$ flows from plate 2, at potential E, to plates 13 at earth potential. In this way a uniform potential gradient is preserved across insulators 9c and 9d, random charges are dispersed and a linear field is maintained between plate 2 and plates 1 and 13 over the whole area of cells $f$ and $e$ and with no edge-effects between plates 1 and 13. Leakage currents between the polarizing and collector plates are prevented by the guard rings, and leakage between plates 1 and 13 is virtually eliminated by keeping them at the same potential. Air turbulence and flow distortion are also avoided since the insulators 9c and 9d are not in the air stream over collector plates 1 and the air channels are sealed over the length of the cell.

Additional features are shown in FIG. 8 which shows the constructional details of one embodiment of the collector plate assembly. Plates 1 and 13 may be constructed in various ways, for instance by depositing a metallic coating on insulating plate 14, or by the use of adhesive foil. Slots 17 may then be cut or milled to give the required electrical separation. As shown, plates 13 are extended round the edge and back of plate 14 to provide electrostatic screening, and a further conductive plate or coating 18 is provided to complete the screening of the collector plate 1. Heater wires 19, secured by tape covering 20, are provided to prevent condensation and to preserve the required high level of insulation resistance in slots 17.

As shown in FIG. 7, errors due to the external field from the polarizing plate 2 are avoided by extending the collector plates beyond the end of plate 2 at the air intake end. The field pattern 21 between plates 1 and 2 at this point is easily calculated for purposes of calibration. External field effects at the exhaust end are unimportant.

The design features incorporated in this invention result in a collector which meets requirements (i) to (v) by the elimination of errors as defined in Table 1.

I claim:

1. An ion counter comprising an electrometer, a collector and a voltage source, wherein said collector comprises insulators, a flat polarizing plate, screening members and a first and a second flat collector plate, said collector plates being spaced by said insulators from and arranged either side of, so as to extend in planes which are substantially parallel to the plane of, said flat polarizing plate so as to form a first and a second air passage between the latter and a respective one of said collector plates, and said screening members are provided along the margins of the air passages with a predetermined insulation resistance between them and the collector plates, the arrangement being such that, in use of the ion counter, said voltage source is connected to maintain said screening members at the same potential as the collector plates, and whereby a substantially uniform potential gradient can be preserved across the insulators, random charges are dispersed and a substantially linear field is maintained between said polarizing plate on the one hand and said collector plates and screening members on the other hand over substantially the whole area of said passages in said planes and with substantially no field edge-effects between said collector plates and said screening members.

2. An ion counter according to claim 1, wherein the insulators have machined faces facing said collector plates and polarizing plate and said plates are tightly secured to said insulators so as accurately to maintain the spacing between said plates.

3. An ion counter according to claim 1, wherein said screening members are in the form of plates arranged coplanar with respective ones of said collector plates.

4. An ion counter according to claim 1, wherein the surfaces of said insulators are coated with a material which renders said surfaces very slightly conductive so that, in use of the ion counter, a very small leakage current flows from said polarizing plate to said screening members.

5. An ion counter according to claim 1, wherein said collector also comprises insulating plates, the latter defining structural members of the collector extending in said planes which are parallel to the plane of said polarizing plate, said collector plates and said screening members each being defined by a metallic coating deposited on said insulating plates.

6. An ion counter according to claim 1, wherein said collector also comprises insulating plates, the latter defining structural members of the collector extending in said planes which are parallel to the plane of said polarizing plate, said collector plates and said screening members each being defined by an adhesive, electrically conducting foil, secured by adhesion to said insulating plates.

7. An ion counter according to claim 1 wherein said collector also comprises insulating plates, the latter defining structural members of the collector extending in said planes which are parallel to the plane of said polarizing plate, each of said screening members extending around the edges and the face, outside its adjacent said air passage, of said insulating plates, so as to provide electrostatic screening, and a further conductive plate or coating is provided on said outside face of each of said insulating plates to complete the screening of said collector plates.

8. An ion counter according to claim 1, wherein said collector also comprises an electrical conductor arranged on each one of insulating plates, the latter defining structural members of the collector extending in said planes which are parallel to the plane of said polarizing plate, outside each of said air passages, said electrical conductors being electrically insulated from said collector plates and screening members, said conductors being adapted, in use of the ion counter, to carry an electric heating current to prevent condensation and to preserve the required high level of insulation resistance between said collector plates and said screening members adjacent thereto.

9. An ion counter according to claim 1, wherein at the inlet sides of said air passages, said collector plates extend beyond said polarizing plate in such a way that the field pattern between said collector plates and said polarizing plate may readily be calculated for purposes of calibration.

10. An ion counter according to claim 1, wherein said potential is earth potential.

* * * * *